United States Patent [19]

Alexander et al.

[11] Patent Number: 5,679,355
[45] Date of Patent: Oct. 21, 1997

[54] VACCINES CONTAINING NON-IONIC SURFACTANT VESICLES

[75] Inventors: James Alexander; James MacDonald Brewer, both of Glasgow, Great Britain

[73] Assignee: Proteus Molecular Design Limited, Cheshire, Great Britain

[21] Appl. No.: 302,915

[22] PCT Filed: Apr. 6, 1993

[86] PCT No.: PCT/GB93/00716

§ 371 Date: Jan. 5, 1995

§ 102(e) Date: Jan. 5, 1995

[87] PCT Pub. No.: WO93/19781

PCT Pub. Date: Oct. 14, 1993

[30] Foreign Application Priority Data

Apr. 7, 1992 [GB] United Kingdom .................. 9207731

[51] Int. Cl.$^6$ .............. A61K 45/00; A61K 9/10; A61K 45/05; A61K 47/00
[52] U.S. Cl. .................. 424/278.1; 424/280.1; 424/450; 428/402.2
[58] Field of Search ................. 424/450, 280.1, 424/278.1; 428/402, 402.2–402.24

[56] References Cited

U.S. PATENT DOCUMENTS

| | | | |
|---|---|---|---|
| 4,772,471 | 9/1988 | Vanlerberghe et al. | 424/450 |
| 4,830,857 | 5/1989 | Handjani et al. | 424/450 |
| 5,171,577 | 12/1992 | Griat et al. | 424/450 |

FOREIGN PATENT DOCUMENTS

| | | |
|---|---|---|
| 0 433 242 A1 | 6/1991 | European Pat. Off. |
| 2 189 457 | 10/1987 | United Kingdom . |
| WO 87/02250 | 4/1987 | WIPO . |
| WO 88/06881 | 9/1988 | WIPO . |
| WO 88/06882 | 9/1988 | WIPO . |
| WO 92/171719 | 10/1992 | WIPO . |

OTHER PUBLICATIONS

Gregory Gregoriadis, "Immunological adjuvants: a role for liposomes", Immunology Today, vol. 11, No 3 1990, p. 89.
Gregory Gregoriadis, Ph.D. "Medical Progress—The Carrier Potential of Liposomes in Biology and Medicine (First of Two Parts)", The New England Journal Of Medicine, Sep. 23, 1976, pp. 704–710.
A. Yekta Ozer et al., "A Novel Drug Delivery System: Non–Ionic Surfactant Vesicles" Eur J. Pharm. Biopharm 37/2 75–79 (1991).
Ruth Lifshitz, et al., "Liposomes as immunological adjuvants in eliciting antibodies specific to the synthetic polypeptide poly (LTyr, LGlu)–poly (DLAla)—poly (LLys) with high frequency of site–associated idiotypic determinants", Eur. J. Immunol. 1981 11:398–404.
A.J. Baillie, et al., "The Preparation and Properties of Niosomes—Non–ionic Surfactant Vesicles", J. Pharm. Pharmacol. 1985, 37:863–868, Received Aug. 29, 1985.

Primary Examiner—James C. Housel
Assistant Examiner—Rodney P. Swartz
Attorney, Agent, or Firm—Pennie & Edmonds

[57] ABSTRACT

Non-ionic surfactant vesicles (NSIV) with entrapped antigen act as potent immunological adjuvants and can produce antibody titers of the same order of magnitude as those using Freund's Complete Adjuvant. The invention provides vaccines comprising such vesicles. Preferably non-ionic surfactants are glycerol esters particularly 1-monopalmitoyl glycerol. The vesicles may be administered by injection or via the mucosal route, oral administration being preferred.

36 Claims, 14 Drawing Sheets

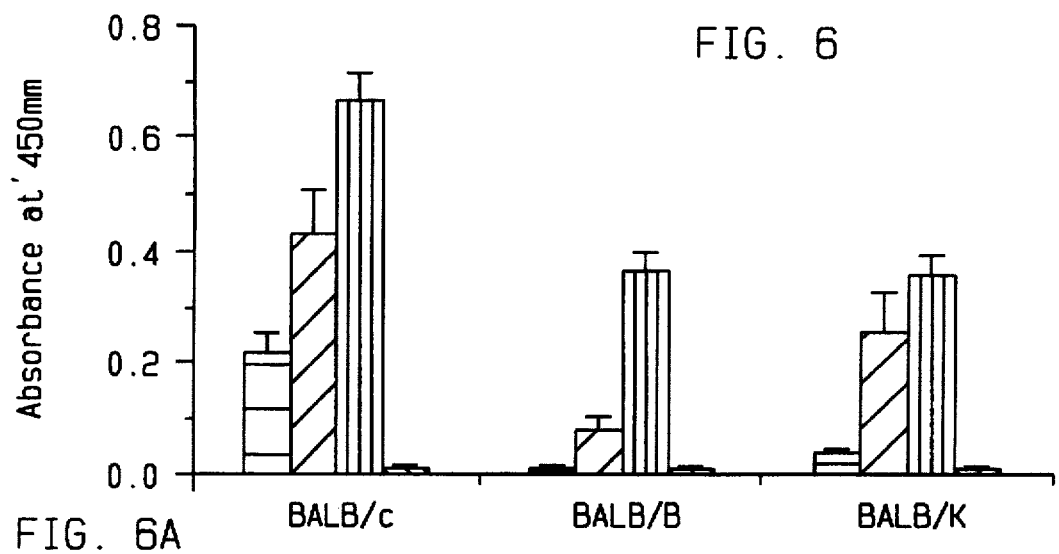
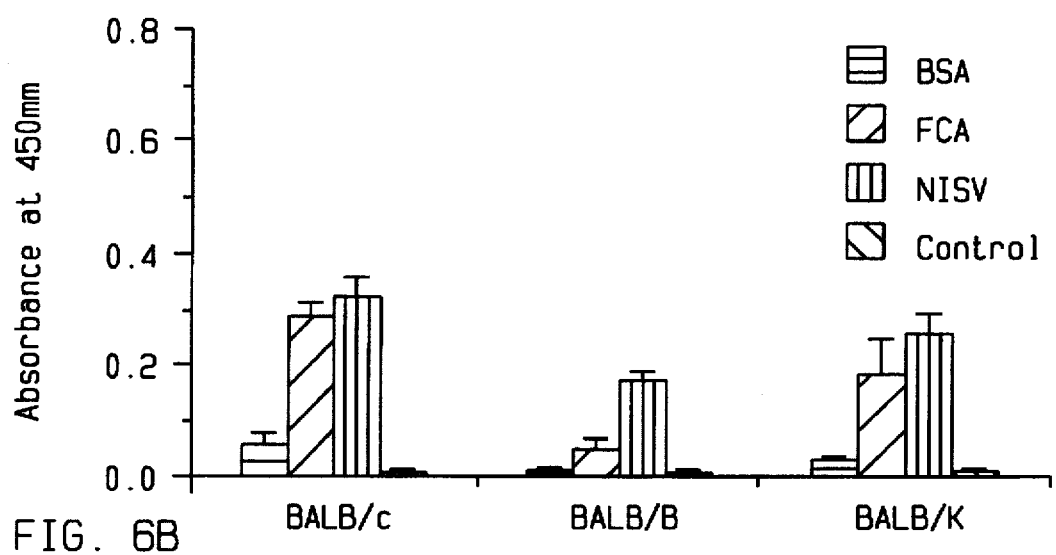
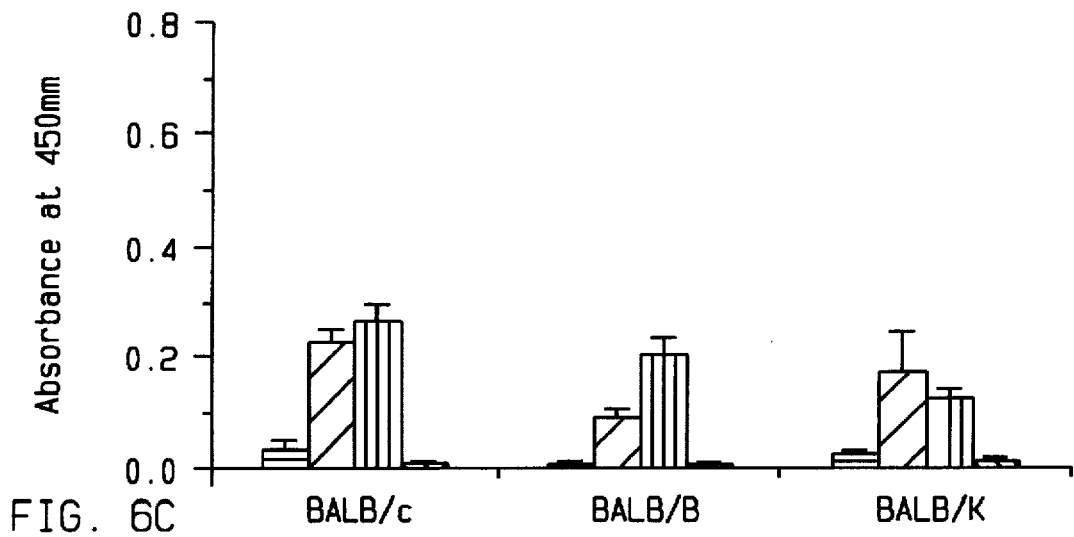
FIG. 6
FIG. 6A
FIG. 6B
FIG. 6C

□ dead
Ⅲ infected
◇ uninfected

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly Ile Leu Glu Ser Arg Gly Ile Lys Ala Arg Ile Thr His Val Asp
 1               5                  10                  15

Thr Glu Ser Tyr
            20
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Glu His Trp Ser Tyr Gly Leu Arg Pro Gly Gly Cys
 1               5                  10
```

VACCINES CONTAINING NON-IONIC SURFACTANT VESICLES

BACKGROUND OF THE INVENTION

This invention concerns improvements in or relating to vaccines and more particularly relates to a novel adjuvant for use e.g. in vaccines containing synthetic antigens.

Many successful human and veterinary vaccines employ attenuated living pathogens. However, recent studies with a whole range of pathogenic infections have identified potentially protective, species-specific antigens which can be produced in bulk using recombinant DNA technology and improved culturing, harvesting and purifying techniques. It is also now feasible to produce wholly synthetic peptide antigens which mimic significant epitopes of a natural antigen. Subunit vaccines are vaccines which contain only certain antigenic parts of the pathogen ie. can include antigenic proteins or individual peptide epitopes. Suitable peptides may be designed by computer modelling techniques. Such synthetic antigens have many potential advantages, including purity, stability, a high level of protection, specificity and a guaranteed lack of any pathogenic properties as are sometimes seen with vaccines containing attenuated pathogens.

Unfortunately, antigens of low molecular weight, whether made by chemical synthesis or by recombinant means, exhibit an inherently low antigenicity; in general, they are weak stimulators of the immune response. Even after conjugation to a carrier protein such as purified protein derivative of tuberculin (PPD) their immunogenicity is often inadequate to elicit an adequate response.

This problem can be overcome by the use of adjuvants, but such adjuvants introduce further difficulties. The only adjuvant currently licensed for use in man is aluminium hydroxide. However aluminium hydroxide is not considered to be an adequate adjuvant for all antigens as it does not boost cell-mediated immunity (CMI), an essential property if a vaccine is to be successful against intracellular pathogens such as Leishmania and Toxoplasma. Freund's Complete Adjuvant (FCA) does stimulate cellular immunity but is unsuitable for human or veterinary use as it promotes granuloma formation, adhesions, and other toxic side effects. FCA also produces a local inflammatory reaction which can persist for months. There is an urgent need for new non-toxic adjuvants which promote cell-mediated immunity (CMI), preferably to a level comparable with that seen with FCA. Indeed, such adjuvants will be essential if the full potential of subunit vaccines is to be realised.

SUMMARY OF THE INVENTION

We have now discovered that non-ionic surfactant vesicles (NISV) with entrapped antigen act as potent immunological adjuvants, even with shorter peptide antigens which inherently provoke a weak immune response. Indeed we have observed antibody titres of the same order of magnitude as and T cell stimulation indices greater than those using FCA as the adjuvant with, however, no evident toxicity. Also, the immune response may be altered qualitatively as well as quantitatively, as discussed more fully later herein.

The best known vesicles are liposomes having a phospholipid bi-layer. However other amphipathic molecules can be made to form vesicles, including non-ionic surfactants (NIS). Indeed such NISV have already been proposed as drug carriers, e.g. for anti-neoplastic agents such as methotrexate and doxorubicin. However, we are not aware of any recognition that NISV are able greatly to potentiate the immunological response to antigens, even when the antigen alone elicits a minimal response, as is the case with peptide antigens.

Thus in one aspect our invention provides a vaccine comprising at least one antigen, especially a peptide of synthetic or recombinant origin, entrapped in NISV.

Another aspect of our invention is a method of potentiating the immunological response, to at least one antigen in a mammalian or non-mammalian subject which comprises administering said at least one antigen entrapped in NISV.

A still further aspect of our invention is a method for preparing a vaccine which comprises entrapping at least one antigen, e.g. a peptide antigen of synthetic or recombinant origin, in NISV.

BRIEF DESCRIPTION OF THE DRAWINGS

FIGS. 1–9 are graphs which illustrate the performance and features of the invention and in which:

FIG. 1 depicts the antibody response of male rats immunized with an LHRH-Gly-Cys-PPD conjugate;

FIG. 2 shows the effect of BCG priming on the antibody response to the LHRH-Gly-Cys-PPD conjugate;

FIG. 3 depicts the end point titre of the immune response of NISV compared to that of FCA;

FIGS. 4a and 4b illustrate the anti-BSA antibody titres for IgG1 and IgG2a;

FIG. 5a shows the total immunoglobulin detected after secondary inoculation, while

FIG. 6 illustrates antibody titres after secondary inoculation, with FIGS. 6A, 6B and 6C illustrating amounts of BSA specific total antibody titres measured 14, 35 and 70 days, respectively, after inoculation.

FIG. 7B illustrates serum antibody levels found in BALB/K mice brains 8 weeks after oral infection for vaccinated and non-vaccinated mice;

FIG. 7C illustrates the mean number of cysts found in BALB/K mice brains 8 weeks after oral infection for vaccinated and non-vaccinated mice;

FIG. 7D illustrates foetal death of pups born to vaccinated and non-vaccinated mice;

FIG. 8 shows the peptide specific T cell proliferative response from spleens of mice immunized with NISV entrapped antigen; and FIG. 9 shows the presence of IFN-γ from spleens of mice immunized with NISV entrapped antigen.

Figure 1:
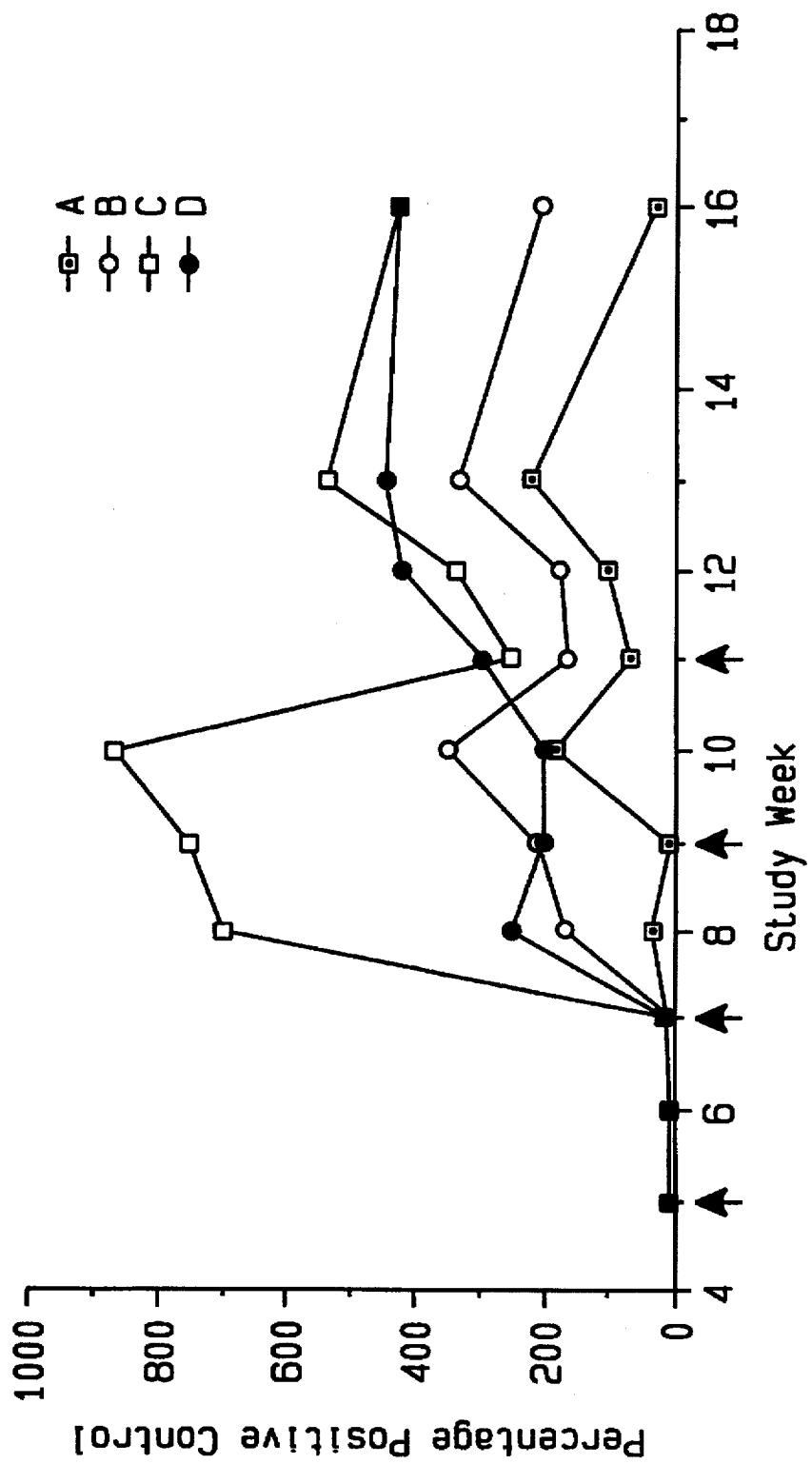

The non-ionic surfactant used to form the NISV may be any pharmacologically acceptable material with the appropriate surface active properties. Preferred examples of such materials are glycerol esters. Such glycerol esters may comprise one or two higher aliphatic acyl groups e.g. containing at least ten carbon atoms in each acyl moiety. Glycerol monoesters are preferred, particularly those containing a $C_{12}$–$C_{20}$ alkanoyl or alkenoyl moiety, for example caproyl, lauroyl, myristoyl, palmitoyl, oleyl or stearoyl. A particularly preferred surfactant is 1-monopalmitoyl glycerol.

Ether-linked surfactants may also be used as the non-ionic surfactant of which the NISV according to the invention are comprised. Preferred examples of such materials are ether-linked surfactants based on glycerol or a glycol preferably a lower aliphatic glycol of up to 4 carbon atoms, most preferably ethylene glycol. Surfactants based on such glycols may comprise more than one glycol unit, preferably up to 5 glycol units and more preferably 2 or 3 glycol units, for example diglycol cetyl ether or polyoxyethylene-3-lauryl ether. Glycol or glycerol monoethers are preferred, particularly those containing a $C_{12}$-$C_{20}$ alkanyl or alkenyl moiety, for example capryl, lauryl, myristyl, cetyl, oleyl or stearyl.

The ethylene oxide condensation products usable in this invention include those disclosed in WO88/06882, i.e. polyoxyethylene higher aliphatic ether and amine surfactants. Particularly preferred ether-linked surfactants are 1-monocetyl glycerol ether and diglycol cetyl ether. However, for use in the present invention it is necessary to select pharmacologically acceptable materials, preferably those which are readily biodegradable in the mammalian system. For this reason, we prefer the aforementioned glycerol esters for preparing vesicles to be administered by injection, either subcutaneous, intramuscular, intradermal or intraperitoneal, or via the mucosal route such as by oral, nasal, bronchial, urogenital or rectal administration, oral administration being particularly preferred.

For effective vesicle formation, the non-ionic surfactant will need to be admixed with an appropriate hydrophobic material of higher molecular mass capable of forming a bi-layer, particularly asteroid, e.g. a sterol such as cholesterol. The presence of the steroid assists in forming the bi-layer on which the physical properties of the vesicle depend.

The NISV may also incorporate a charge-producing amphiphile, to cause the NISV to take on a negative charge. Acidic materials such as higher alkanoic and alkenoic acids (e.g. palmitic acid, oleic acid); or other compounds containing acidic groups, e.g. phosphates such as dialkyl, preferably di(higher alkyl), phosphates, e.g. dicetyl phosphate, or phosphatidic acid or phosphatidyl serine; or sulphate monoesters such as higher alkyl sulphates, e.g. cetyl sulphate, may all be used for this purpose.

The steroid may e.g. comprise 20-120 percent by weight of the non-ionic surfactant, preferably 60-100 percent. The amphiphilic material producing a negative charge may e.g. comprise 1-30 percent by weight of the non-ionic surfactant.

The charge-producing amphiphilic material stabilises the structure of the vesicles and provides effective dispersion.

The non-ionic surfactant and membrane-forming hydrophobic material may be converted to NISV by hydration in the presence of shearing forces. Apparatus to apply such shearing forces is well known, suitable equipment being mentioned e.g. in WO88/06882. Sonication and ultrasonication are also effective means to form NISV or to alter their particle size.

An effective method for the production of NISV is that disclosed by Collins et al, *J. Pharm. Pharmacol.* 42, 53 (1990). This involves melting a mixture of the NIS, steroid, and amphiphile (if used) and hydrating with vigorous mixing in the presence of aqueous buffer. The suspension may then be extruded several times through microporous polycarbonate membranes at an elevated temperature sufficient to maintain the NISV-forming mixture in a molten condition.

It is also possible to form NISV by rotary film evaporation from an organic solvent, e.g. a hydrocarbon or chlorinated hydrocarbon solvent such as chloroform. The resulting thin film may then be hydrated in phosphate-buffered saline in the presence of the antigen and optionally another surfactant (Russell and Alexander, *J. Immunol.* 140, 1274 (1988)). In the case where antigen is entrapped within the NISV during their formation, extravesicular antigen may be removed from the vesicle suspension by washing using known methods of separation, such as by gel filtration or centrifugation, e.g. ultracentrifugation.

Methods by which antigens may be entrapped within preformed NISV are the dehydration-rehydration method (Kirby and Gregoriadis, Biotechnology 2, 979 (1984)) in which antigen present in the aqueous phase is entrapped in pre-formed vesicles by flash freezing followed by lyophilisation, and the freeze-thaw technique (Pick, Arch. Biochem. Biophys. 212, 195 (1981)). In the latter technique, vesicles are mixed with antigen and repeatedly flash frozen in liquid nitrogen and e.g. warmed to temperatures of the order of 60° C. (i.e. above the transition temperature of the relevant surfactant).

The vesicles may be further processed to remove any non-entrapped antigen e.g. by washing and centrifuging. It should be noted that our results clearly show that the NIS alone are not an effective adjuvant, i.e. vesicular formation is essential to obtain the desired effect. The antigen must be entrapped within the NISV if the desired adjuvant effect is to be achieved.

The antigen is preferably a peptide of synthetic or recombinant origin containing e.g. from 8-50, preferably from 10-20 amino acid units. The antigen may e.g. mimic one or more B cell, or B cell and T cell epitopes of a pathogenic organism, so that the vaccine elicits neutralising antibodies against that organism (see, for example, the disclosure of synthetic antigens to HIV in our WO88/10267 and WO91/13909).

Alternatively, the peptide may elicit an immune response against another biologically active substance, particularly a substance having hormonal activity. An example in the latter category would be the induction of an immune response against endogenous luteinising hormone-releasing hormone (LHRH). Such treatment can e.g. be used for androgen suppression or immuno-castration of farm animals and for the treatment of androgen-sensitive or oestrogen-sensitive carcinoma (see our GB-B-2196969). The peptide antigen will itself often exhibit sufficient immunogenicity for use as a vaccine when entrapped in NISV; this is particularly the case when the peptide contains well-recognised epitopes, and comprises at least about 12, preferably at least 15, amino-acid residues.

In some cases it may be desirable to link the peptide to a carrier to boost its immunogenicity. Suitable carriers are well known in the art, e.g. protein carriers such as purified protein derivative of tuberculin (PPD), tetanus toxoid, cholera toxin and its B subunit, ovalbumin, bovine serum albumin, soybean trypsin inhibitor, muramyl dipeptide and analogues thereof, and Braun's lipoprotein. When using PPD as the carrier, a higher titre of antibodies is achieved if the recipient of the vaccine is already tuberculin sensitive, e.g. by virtue of earlier BCG vaccination.

The antigen(s) entrapped in NISV may be formulated into a vaccine using conventional methods of pharmacy, such as by suspension in a sterile parenterally-acceptable aqueous vehicle.

Although synthetic or recombinant peptides are the preferred antigens for use in this invention, a strong adjuvant effect is also observed when protein antigens are entrapped in NISV. For example, strongly positive results have been obtained using bovine serum albumin (BSA) as the antigen; more significantly, effective protection against toxoplasmosis has been established by immunisation with the supernatant of disrupted cells of *Toxoplasma gondii*, using an NISV adjuvant.

We have found that subcutaneous inoculation is often the most effective mode of administration by injection and in particular may often be more effective than intraperitoneal administration. Intramuscular or intradermal injection is effective, perhaps because it results in the formation of an antigen depot at the site of injection. However the injection site did not exhibit the chronic inflammatory reaction which FCA notoriously produces. Administration by injection induces a systemic immune response, i.e. both a humoral and cell-mediated immunity. Immunisation at one mucosal surface (e.g. nasal) is expected to result in a mucosal immune response at other mucosal surfaces (e.g. bronchial). The vaccine according to the invention may also be administered via the mucosal route.

According to another surprising and valuable feature of our invention, antigens entrapped in NISV often exhibit a useful level of immune response when administered by the oral route. The NISV appear to be able to protect an antigen from digestion in the gastrointestinal tract, at least to some extent, and to pass through the wall of the gut unchanged, thus giving results hitherto only obtainable on parenteral administration.

Our invention therefore provides a method of formulating an antigen as an orally-active vaccine which comprises entrapping said antigen in NISV.

The ability to achieve an adjuvant effect by oral administration e.g. of a synthetic peptide is a highly beneficial property of the vaccines of the present invention, and is a property that has not previously been contemplated in the prior art. The oral administration route has several advantages over the previous administration routes of injection. Dangers of infection which accompany injection such as, for example, derive from the use of non-sterile needles, are avoided. In addition to inducing a systemic immune response, oral administration may also induce a mucosal response. Such a mucosal response is thought to be important in immunological protection against many pathogens, e.g. HIV, *Toxoplasma*. Acceptability to patients is also higher for oral compositions.

In formulating vesicles to be used as vaccines specifically to be orally administered, ester-linked surfactants are preferred, although ether-linked surfactants particularly 1-monocetyl glycerol ether and diglycol cetyl ether may be used. Ether linkages have been found to be more acid stable than corresponding ester linkages and are believed to have a greater ability to withstand degradation in the acid environment of the mammalian stomach.

Further analysis of the immune response produced by the novel vaccine of this invention has shown, surprisingly, that a high proportion of the antibodies are of the IgG2a type, associated with the release of IL-2 and IFN-γ. These cytokines are secreted by the Th1 subset of CD4+ T lymphocytes. High IgG2a levels are believed to be associated with the development of cell-mediated immunity (CMI). On the other hand aluminium hydroxide preferentially stimulates Th2 cells, resulting in the production of IgG1 antibodies, and Freund's Complete Adjuvant, although generally associated with heightened cell-mediated immunity, also produces high and prolonged IgG1 titres. The Th2 cells are the primary regulators (via IL-4 secretion) of not only IgG1 but also IgE synthesis. Thus sustained production of high levels of IgG1 in the plasma may not be desirable as it may also indicate over-production of IgE. Recent in vitro studies have established that Th1 and Th2 cells have different antigen-processing requirements. Th1 cells require antigen presentation by macrophages whereas Th2 cells are optimally stimulated by B-cell presentation (Gajewski et al, *Immunol. Rev.* III, 79, (1989) and Gajewski et al, *J. Immunol.* 146, 1750, 1991). Macrophages appear to be capable of ingesting liposomes and hence encapsulation of antigen inside a vesicle will favour Th1 activation and synthesis of IgG2a antibodies, with a resulting high level of CMI.

Our results have shown that the novel vaccines according to the invention are able to induce titres of IgG2a which are initially greater than those produced by FCA but which over a course of time are ultimately comparable to those produced by FCA. The initial response to vaccines according to the invention appears to be a preferential stimulation of Th1 lymphocytes as compared to Th2 lymphocytes when compared to that chieved by FCA. Our results have also shown that the induced titres of IgG1 achieved using the vaccines of the present invention are in the order of those produced with FCA and accordingly the vaccines of the invention are also useful in mediating humoral immunity.

Thus a further aspect of our invention is a method of formulating at least one antigen to stimulate antibody production via the Th1 T lymphocyte pathway which comprises entrapping said at least one antigen in NISV.

The antigens formulated according to the invention also stimulate antibody production via the Th2 T lymphocyte pathway. The antigens may be formulated to preferentially stimulate antibody production via the Th1 T lymphocyte pathway in comparison to the Th2 lymphocyte pathway, particularly as compared to antibody levels produced using FCA adjuvant.

Moreover, the titres of antibodies elicited by immunisation with NISV-potentiated antigens can actually be higher than those obtained using FCA, while avoiding completely the strong toxic effects of FCA. Thus a still further aspect of our invention is a method for potentiating the immunogenicity of at least one antigen to a level at least equal to that obtained by use of Freund's Complete Adjuvant, which comprises entrapping said at least one antigen in NISV.

NISV appear to be ideal adjuvants for use in vaccines against those diseases requiring cellular or humoral immunity. Another major advantage of NISV as adjuvants particularly those comprising ether-linked surfactants is their stability under typical ambient conditions. In particular they do not undergo destructive autoxidation reactions in the same manner as liposomes based on egg lecithin.

A further important advantage of NISV as adjuvants for use in vaccines is that contrary to the prior art adjuvants, NISV are substantially non-toxic. We have found that intraperitoneal injection into rats of the LHRH analogue LHRH-Gly-Cys (as described in our EP-A-0293530) entrapped within vesicles comprising 1-monopalmitoyl glycerol ester did not cause any toxic side effects, particularly those which are often associated with Freund's Complete Adjuvant or even aluminium gels. No detectable pathology was observed in the test animals.

The above-mentioned EP-A-0293530 describes LHRH analogues of formula pGlu-His-Trp-Ser-Tyr-X-Leu-Arg-Pro-Gly-Y-Z wherein X represents Gly or a D-amino acid, Y represents one or more amino acid residues, which may be the same or different, and Z represents Cys or Tyr, such that the solution conformation of said analogue is substantially similar to that of native LHRH. The analogue LHRH-Gly-Cys is represented as Seq. I.D. No. 2.

The vaccines contemplated by this invention are primarily applicable to mammals and are thus applicable in the fields of human and veterinary medicine. It is also envisaged that NISV can provide an effective adjuvant for some non-mammalian vaccines such as, for example, for vaccination of fish and poultry.

The following Examples illustrate the adjuvant properties of NISV.

EXAMPLES

Example 1

Immunisation of Rats with LHRH-Gly-Cys-PPD NISV Formation

Vesicles were formed from a mixture of the non-ionic surfactant, cholesterol and dicetyl phosphate (Sigma, Poole, Dorset, UK) in the molar ratio 5:4:1. The number of μ moles and weight in mg are shown below:

| Composition of NISV | Moalr ratio | μmoles | weight (mg) |
|---|---|---|---|
| 1-monopalmitoyl glycerol | 5 | 10 | 3.32 |
| cholesterol | 4 | 8 | 3.09 |
| dicetyl phosphate | 1 | 2 | 1.09 |
| Total | 10 | 20 | 7.5 |

Vesicles were formed by the technique of Collins et al (supra). Vesicle preparations were subsequently sonicated for 5 min at 20° in a Mettler Electronics water-bath sonicator (50 Hz, Pasadena. Calif.). The antigen, LHRH-Gly-Cys, an analogue of luteinising hormone-releasing hormone, is described in our EP-A-0293530. Antigen entrapment into preformed vesicles was achieved by the dehydration-rehydration technique as described by Kirby and Gregoriadis (Biotechnology, 2, 979 (1984)). Briefly, 5 ml (150 μmol) of vesicle solution were mixed with 1 ml antigen in PBS (0.5 mg/ml) in polypropylene centrifuge tubes (Elkay Products Inc., Shrewsbury, Mass.) and flash frozen as a thin shell by swirling in liquid nitrogen. Preparations were then lyophilized in a freeze drier at 0.1 torr overnight before rehydration in 0.5 ml distilled water. The samples were left to stand for 30 min and then made up to 6 ml with distilled water.

a) Immunisation with LHRH-Glys-Cys-PPD with and without BCG priming and adjuvants Eight groups of male Copenhagen Fisher F₁ hybrid rats were injected intraperitoneally with 0.2 ml LHRH-Gly-Cys-PPD in phosphate buffered saline, LHRH-Gly-Cys-PPD entrapped in NISV, an emulsion of LHRH-Gly-Cys-PPD in FCA and LHRH-Gly-Cys-PPD adsorbed onto aluminium hydroxide. The quantity of LHRH-Gly-Cys in each injection load was 50 μg with saline, FCA/FIA and alum and 5 μg with NISV.

Four groups of rats were given a primary injection of BCG 4 weeks prior to the first injections with the LHRH-Gly-Cys-PPD conjugate. Four injections with the conjugate were given in total at two-weekly intervals.

Determination of anti-LHRH antibody

Plasma samples obtained at intervals were assayed for anti LHRH antibody by ELISA. Tissue culture grade 96-well microtitre plates were coated with LHRH-Gly-Cys-BSA (in PBS, pH 7.2) at 0.1 μg/well and incubated for 1 hour at 37° C. Wells were washed three times with PBS/0.1% Tween buffer then blocked with 200 μl 3% Marvel/Tween for 1 hour at 37° C. Wells were washed as above and 50 μl samples diluted in PBS were added to duplicate wells. Samples were incubated for 1 hour at 37° C. and the wells were washed as before. Aliquots of 50 μl of horseradish peroxidase goat anti-rat IgG conjugate (Sigma), diluted to 1:5000 in PBS, were added to each well and incubated for 45 minutes at 37° C. before washing as above. Substrate solution was prepared by addition of 4 μl of hydrogen peroxide and 250 μl of stock tetramethyl benzidine in dimethyl sulphoxide (6 mg/ml) to 25 ml of 0.1M acetate-citrate buffer, pH 5.5.

Each well had 100 μl of substrate added before incubation at room temperature in the dark for 5 minutes. The reaction was stopped by addition of 10% sulphuric acid (v/v) and the absorbance at 450 nm was measured. The ELISA results are expressed as a percentage of a positive control. A constant standard was used throughout the assays to enable inter-and intra-comparisons to be made. The constant standard is a pool of serum from a number of rats immunised with LHRH-Gly-Cys-PPD in FCA. This positive control has an arbitrary value of 100%.

Results

Figure 2:
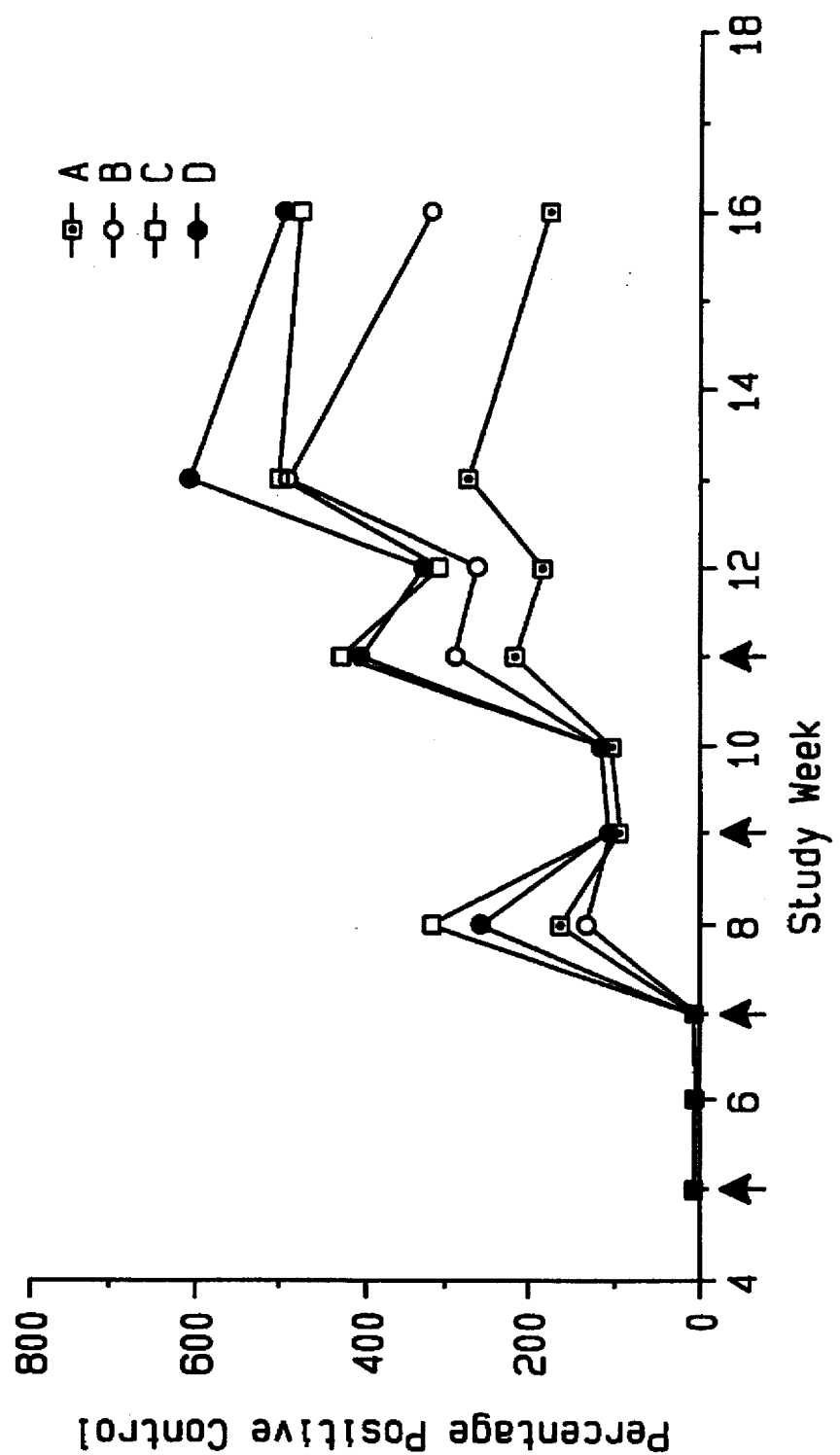

The results of the ELISAs are shown in FIGS. 1 and 2. FIG. 1 depicts the antibody response of Copenhagen-Fisher male rats immunised with the LHRH-Gly-Cys-PPD conjugate in saline (A), niosomes (B), Freund's Complete and Incomplete Adjuvant (C) and aluminium hydroxide (D). Although the antibody responses to LHRH-Gly-Cys appear greater when FCA/FIA or alum are used, the amount of peptide administered with these adjuvants is 10 fold more than that incorporated into the NISV. Thus, NISV appear to have a more potent effect at adjuvanting lower quantities of peptide conjugates than either aluminium hydroxide or Freund's Complete Adjuvant. FIG. 2 shows the effect of BCG priming on the antibody response to the LHRH-Gly-Cys-PPD conjugate. A similar magnitude of immune response is seen both with and without priming. Again the resultant antibody titres are higher with FCA and alum; however, ten times the amount of immunogen was administered with these adjuvants than with NISV.

b) In order to more accurately demonstrate the adjuvant effect of NISV, the antibody response to equivalent amounts of antigen was measured in BALB/c mice injected with LHRH-Gly-Cys-PPD in FCA and within NISV vesicles prepared as described above.

Immunisation with LHRH-Gly-Cys-PPD 3 female BALB/c mice were injected subcutaneously with 0.2 ml LHRH-Gys-Cys-PPD in FCA (1:1 v/v conjugate in PBS:FCA). The mice were boosted by subcutaneous injection two weeks later with 0.2 ml LHRH-Gly-Cys-PPD in FIA (1:1 v/v conjugate in PBS:FIA).

5 female BALB/c mice were similarly subcutaneously injected with 0.2 ml LHRH-Gys-Cys-PPD entrapped in NISV and boosted 2 weeks later with a further 0.2 ml. No BCG priming was used. Each injection administered the equivalent of 100 μg LHRH-Gly-Cys-PPD.

Determination of Anti-LHRH Antibody

Tail bleeds were taken 1 week after the second immunisation, serum samples were pooled and the total antibody response measured by ELISA essentially as described above, but using a serial dilution to establish the end point titre.

Results

Figure 3:
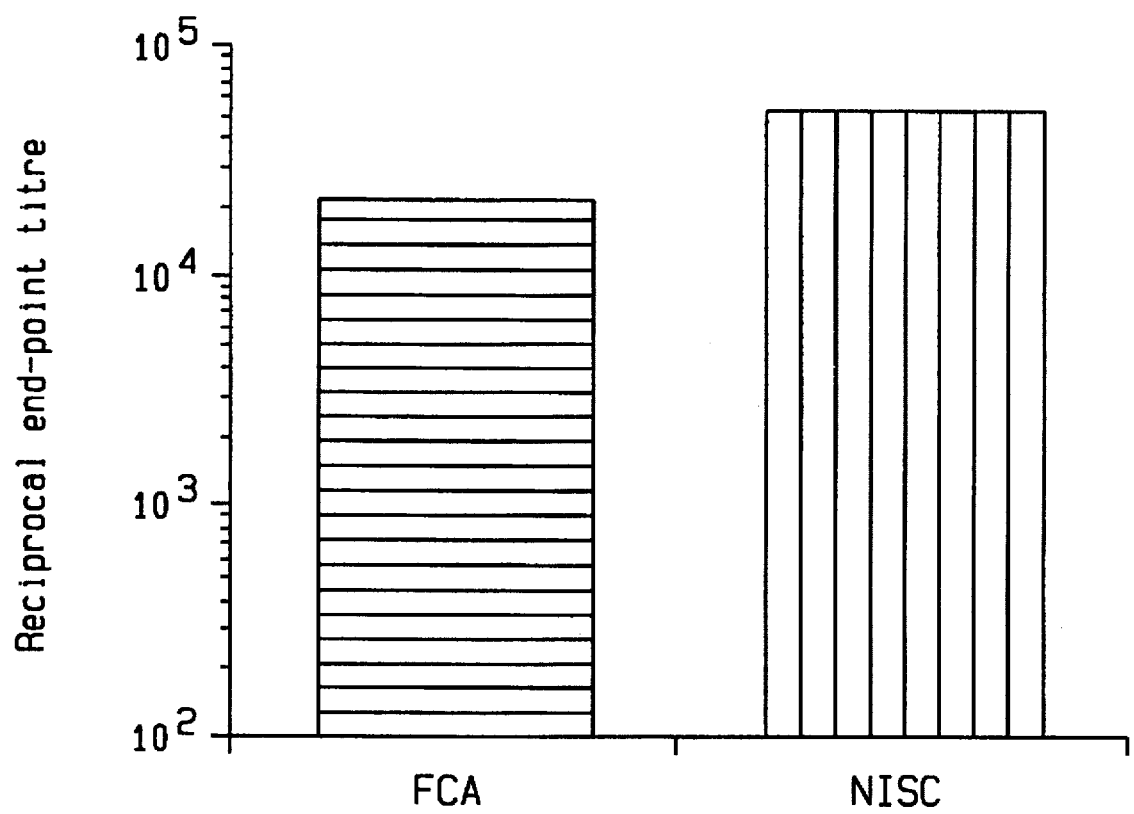

The results are shown in FIG. 3. It can clearly to seen that at equal immunological challenge, NISV is a potent adjuvant, and is capable of inducing an LHRH specific antibody level greater than that achieved with FCA. KEY TO FIGS. 1 AND 2:

A: No adjuvant (saline)
B: Niosomes
C: FCA & FIA
D: Aluminium hydroxide
Arrows show the times of immunisation
FIG. 1: LHRH-Gly-Cys-PPD
FIG. 2: BCG+LHRH-Gly-Cys-PPD
FIG. 3: LHRH-Gly-Cys-PPD Example 2

Immunisation of Mice with Bovine Serum Albumin (BSA)

Vesicles were formed from the components described in Example 1 by the methods described in Example 1 or alternatively by rotary film evaporation from chloroform. The resulting film was hydrated in PBS and antigen (5 mg/ml) or with detergent (1% n-octyl β-D-glucopyranoside, Sigma) and antigen (5 mg/ml) in PBS as described for liposomes by Russell and Alexander (supra). To remove detergent (if used) and any unentrapped antigen, the preparations were centrifuged at 84,000 g for 40–45 min and the pellet resuspended in PBS. Washing was repeated twice.

8–10 week old BALB/c mice were used with four to five mice in each group. On Day 1, groups of mice were injected subcutaneously or intraperitoneally with NISV with entrapped BSA (NISV/BSA), or with an emulsion of BSA in FCA (FCA+BSA: Sigma). The final BSA concentration in each injection was 0.5 mg/ml and each mouse received a 100 μg dose of BSA. Mice were given a primary injection fourteen days before a secondary challenge. Days 14, 28, etc., in the histograms in FIG. 4 refer to the time after secondary challenge.

Figure 4A:
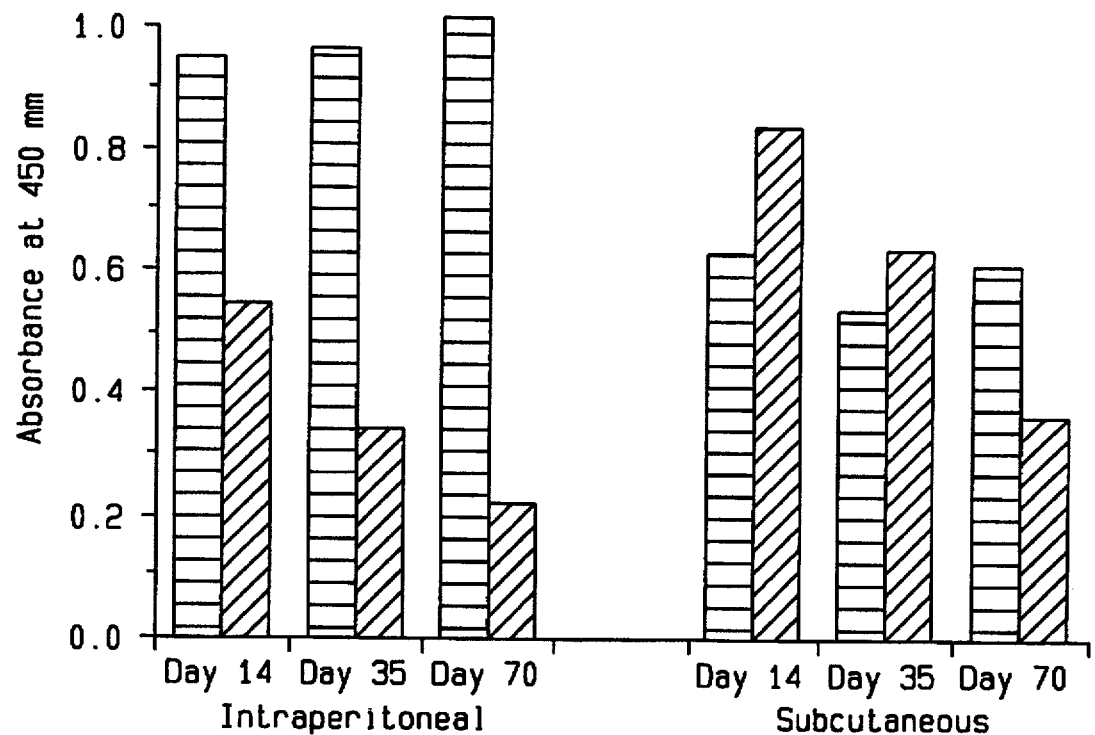
Figure 4B:
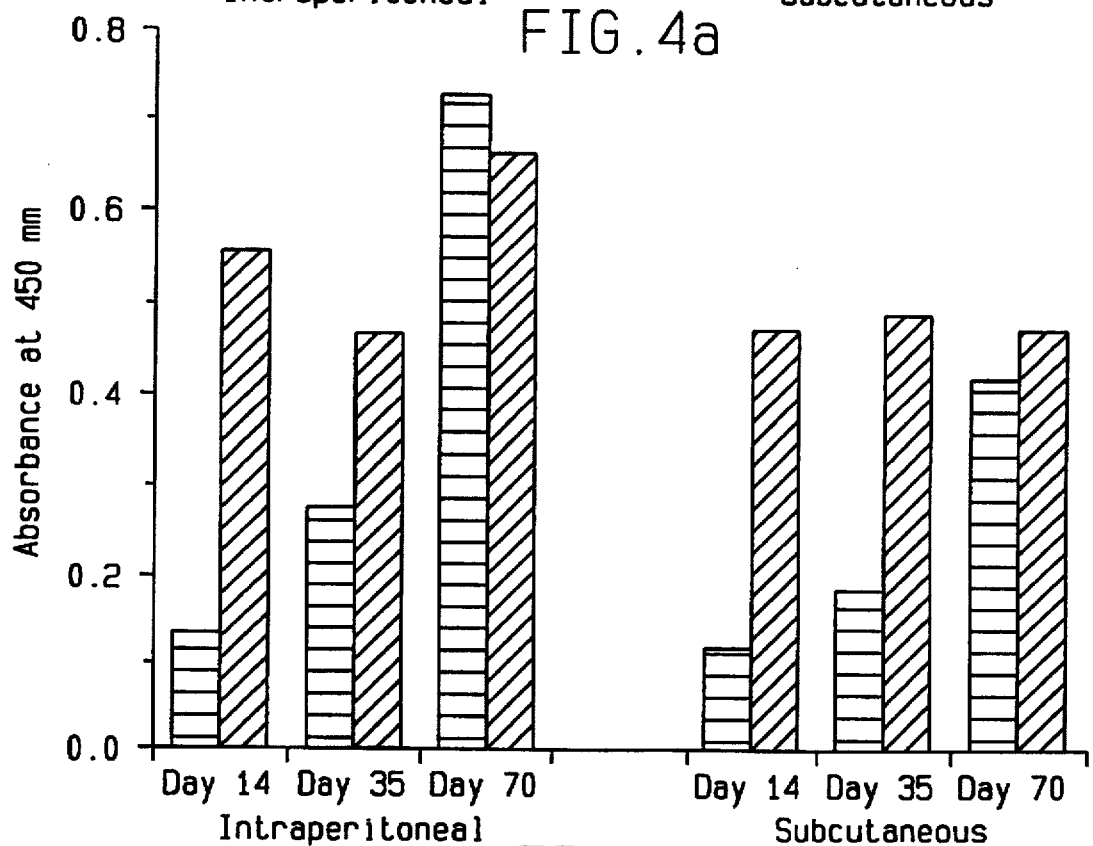

The levels of anti-BSA antibodies were determined by ELISA. In FIG. 4, Section (a) represents antibody titres for IgG1, and Section (b) shows the titres for IgG2a. The cross-hatched histograms refer to NISV/BSA and the solid histograms refer to BSA+FCA. In each case of (a) and (b) the histogram on the left of the figure represents results obtained with intraperitoneal injection, and the histogram on the right represents results obtained from subcutaneous injection.

It will be seen that by intraperitoneal inoculation, FCA+BSA produced very high titres of IgG1 which were maintained up to day 70; with NISV/BSA there was a time-dependent decrease in the titres. By subcutaneous administration, the NISV/BSA immunisation initially produced higher titres than FCA, but by day 70 these had decreased well below the titre obtained with FCA+BSA.

By contrast, the assay for IgG2a in Section (b) shows that NISV/BSA by either intraperitoneal or subcutaneous routes elicited initial titres well above those given by FCA+BSA, but by day 70, due to the time-dependent increase in IgG2a levels produced by FCA+BSA, the titres produced by both adjuvant formulations were similar.

It was noticeable that granuloma formation, observed after subcutaneous injection of FCA, was totally absent after injection of NISV.

Example 3

Adjuvant Activity of NISV Prepared from Various Surfactants

Figure 5A:
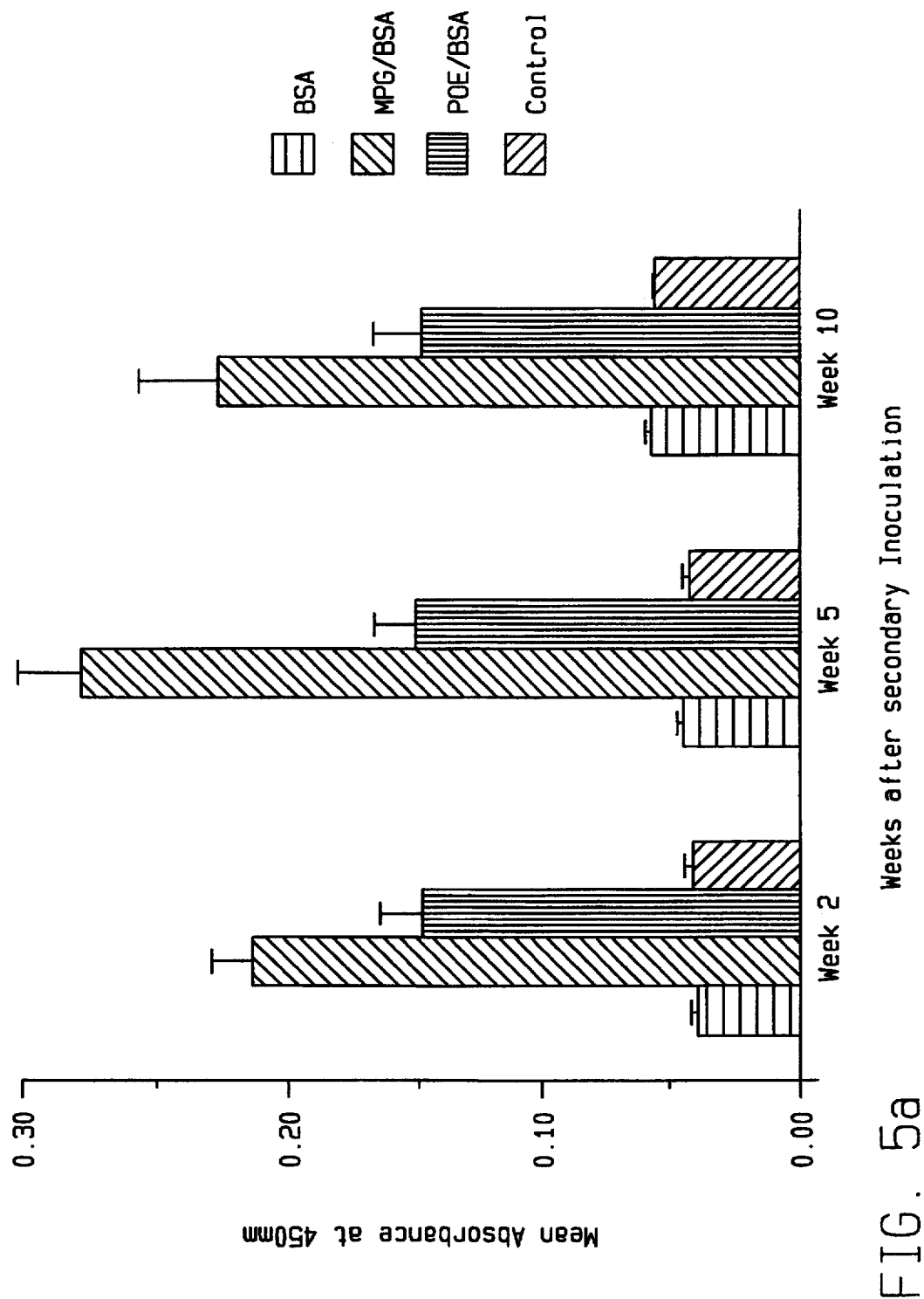
Figure 5B:
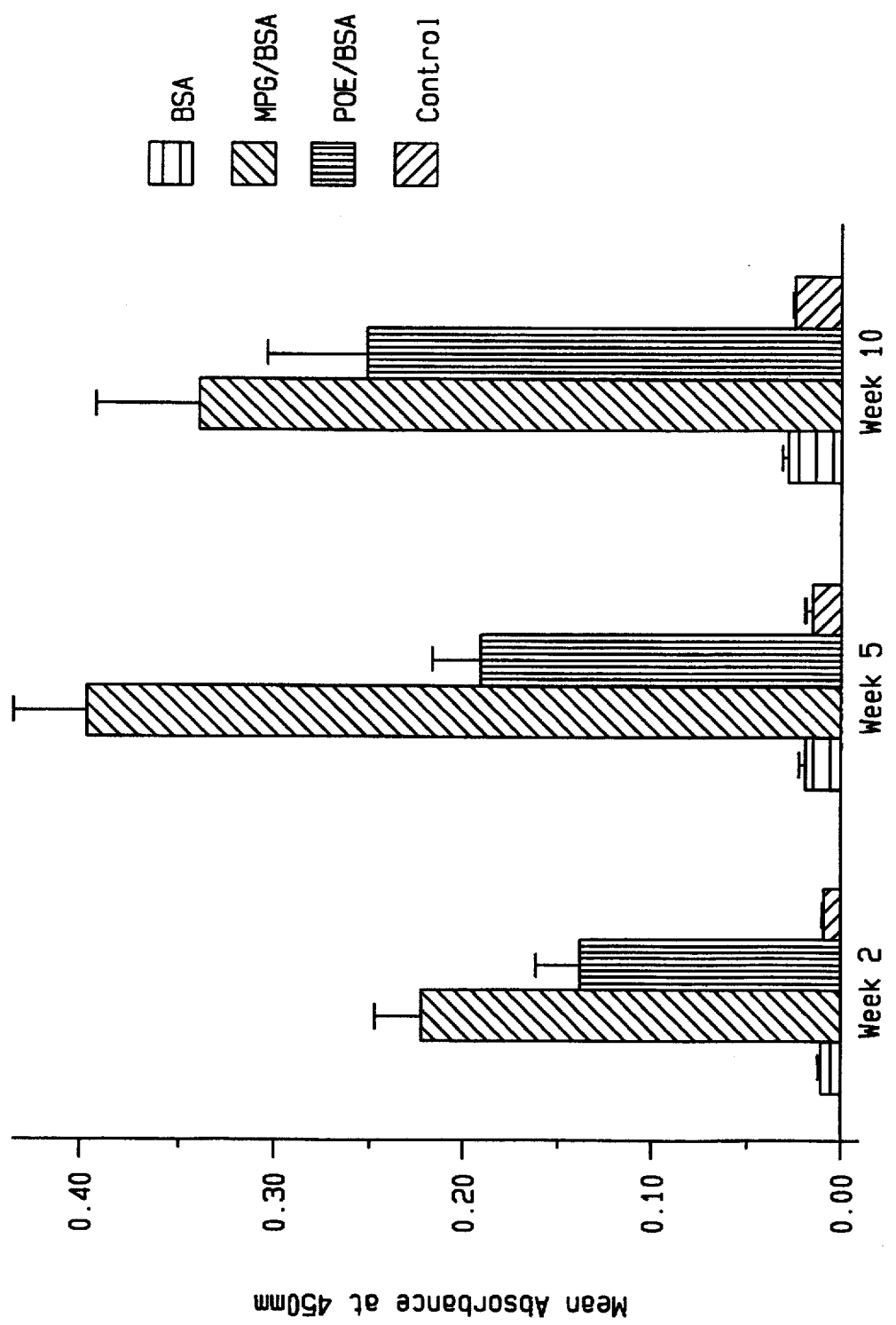
FIGS. 5b and 5c show IgG1 and IgG2a levels, respectively.
Figure 5C:
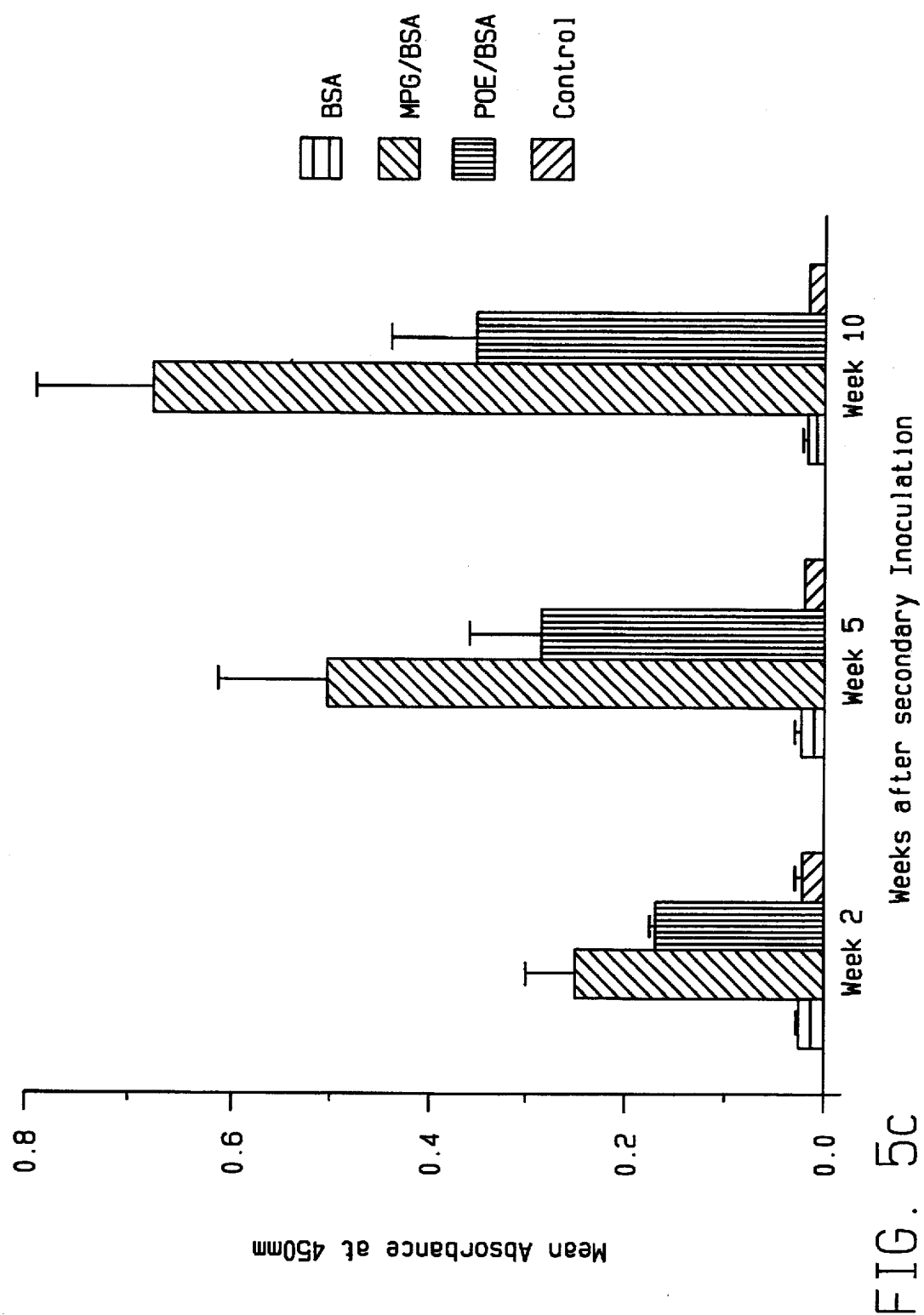

NISV were formed from either a) 1-monopalmitoyl glycerol (MPG) (as in Examples 1 and 2) or b) polyoxyethylene-3-lauryl ether (POE), in the ratio 5:4:1 surfactant:cholesterol:dicetyl phosphate as described in Example 1. Groups of 8–10 week old female BALB/c mice, 5 mice in each group, were injected on day 1 subcutaneously with either BSA entrapped within NISV or in solution in PBS, in the manner described in Example 2. Total Ig, IgG1 and IgG2a levels were assayed by ELISA at 14, 35, and 70 days after the secondary challenge. For the analysis, plasma was diluted 1/8000 for total antibody titre analysis, 1/15000 for IgG1 and 1/1000 for IgG2a and the antibody titres present in the plasma of individual mice were expressed as absorbances detected by ELISA. The results obtained are shown in FIG. 5, in which FIG. 5a shows total immunoglobulin detected at various times after secondary inoculation; FIGS. 5b and 5c show IgG1 and IgG2a levels respectively.

It will be seen that NISV produced from each surfactant significantly enhanced the antibody titres to encapsulated BSA as compared to BSA without adjuvant. For all antibody subclasses analysed, BSA entrapped MPG-based vesicles produced higher antibody titres than BSA entrapped in POE-based vesicles 14 days after secondary injection. By 35 days after secondary infection, Ig and IgG1 titres were higher with MPG than POE based vesicles, however IgG2a levels were similar. By 70 days, there were no significant differences between either vesicle preparation in the titres of total antibody, or either of the immunoglobulin subclasses analysed.

Thus it can be seen that the adjuvant activity of NISV is widely applicable and is not dependent upon any one surfactant.

Example 4

Adjuvant Activity of NISV in Congenic Strains of Mice

Figure 6D:
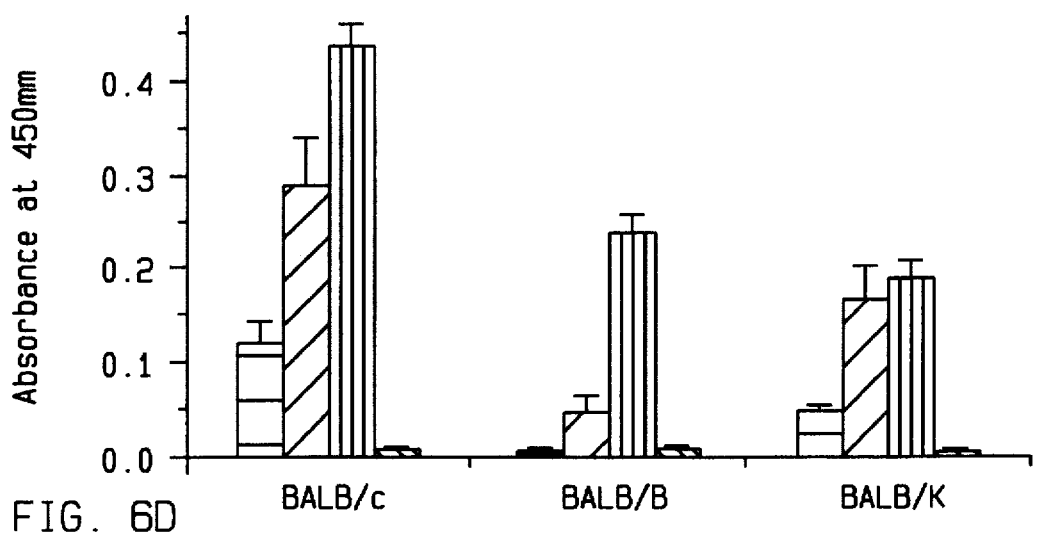
FIGS. 6D, 6E, and 6F illustrating the IgG1 titres measured 14, 35 and 70 days, respectively, after inoculation.
Figure 6E:
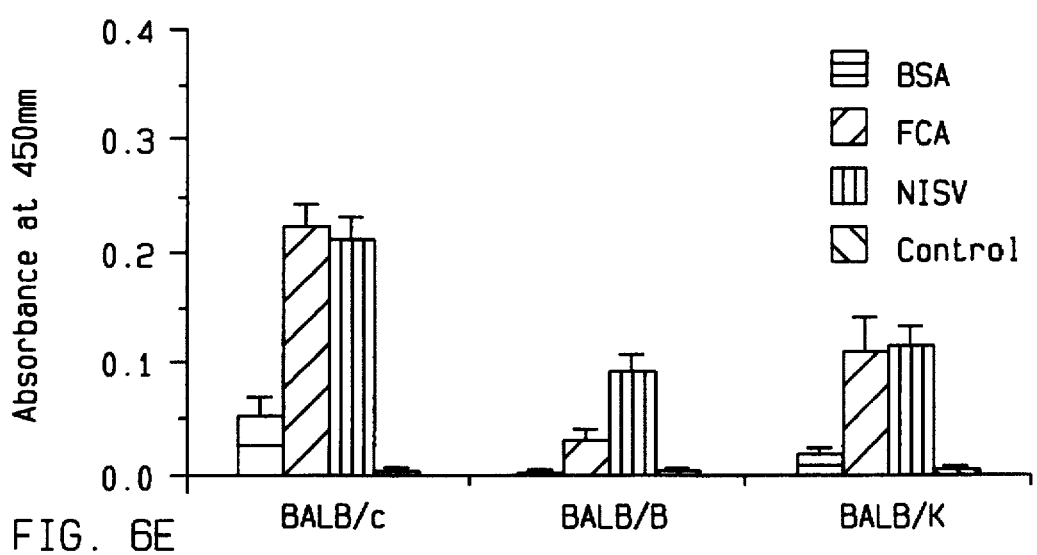
Figure 6F:
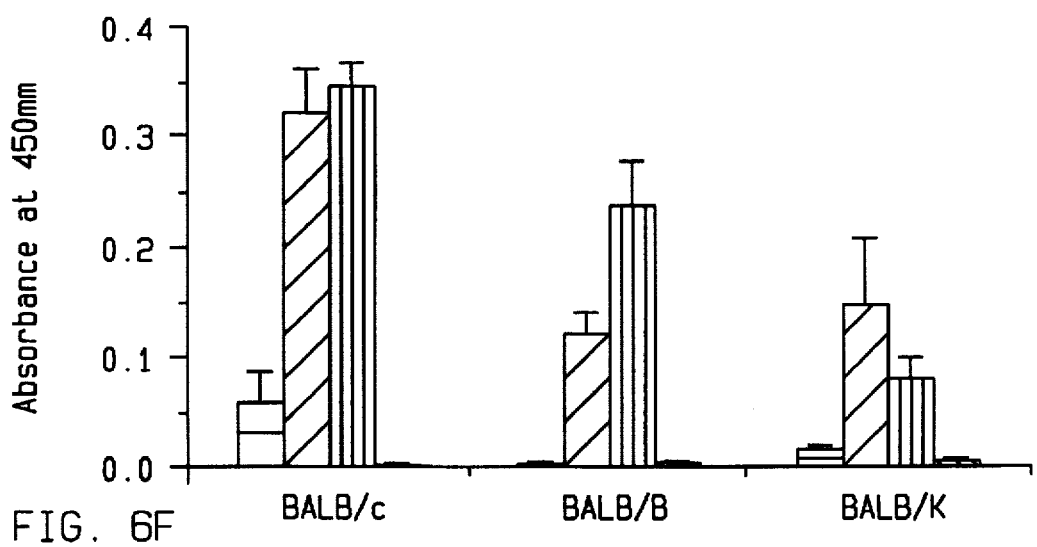

Certain prior art adjuvants are known to have a restricted utility with respect to genetically determined differences in the immune response between individuals. In order to demonstrate that the adjuvant activity of NISV is not limited genetically, the antibody response to BSA administered alone (i.e. in PBS), entrapped in NISV or in an emulsion with Freund's Complete Adjuvant was measured in three strains of BALB mice, BALB/c, BALB/B and BALB/K. NISV were prepared and injected subcutaneously into these groups of mice in accordance with Examples 1 and 2. Antibody levels were measured by ELISA and the results are shown in FIG. 6. In FIGS. 6A, 6B, and 6C, BSA specific total antibody titres are shown as detected in plasma prepared from blood collected 14 days (FIG. 6a), 35 days (FIG.

Figure 6G:
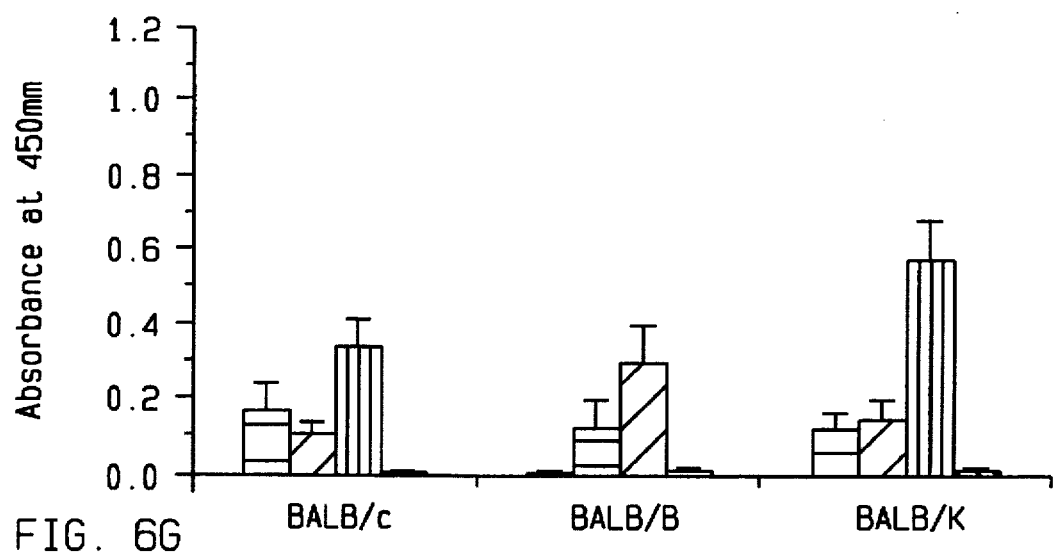
FIGS. 6G, 6H and 6I illustrating the IgG2 titres measured 14, 35 and 70 days, respectively, after inoculation.
Figure 6H:
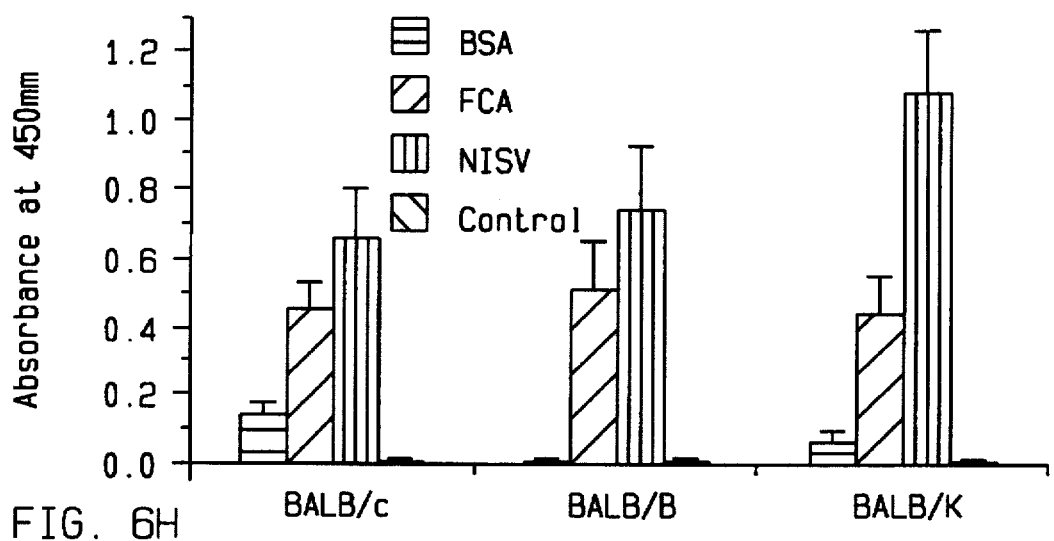
Figure 6I:
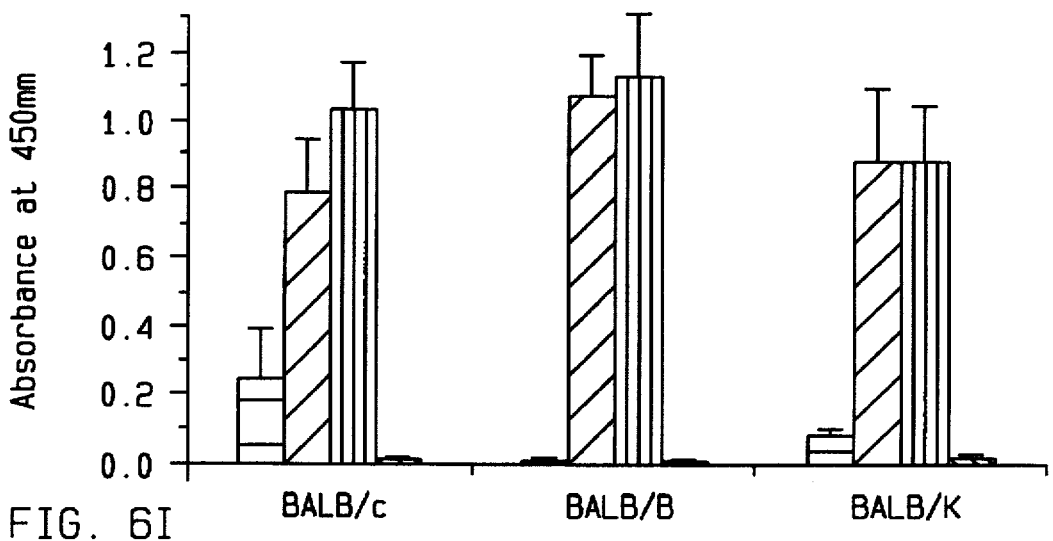

6b) and 70 days (FIG. 6c) after secondary inoculation, where the results are expressed as mean absorbances (+/− S.E) detected at 450 nm. Similar data is shown for IgG1 (FIGS. 6D, 6E, and 6F), and IgG2a (FIGS. 6G, 6H, and 6I). For the ELISA, plasma samples were diluted 1/1500 and conjugate used at dilution 1/1000 (FIGS. 6A, 6B, and 6C), and corresponding figures for plasma and conjugate respectively were 1/30000 and 1/8000 (FIGS. 6D, 6E, and 6F) and 1/1000 and 1/800 (FIGS. 6G, 6H and 6I).

It will be seen that for all mouse strains, NISV/BSA produced high titres of antibody, in respect of both total antibody and the specific isotypes IgG1 and IgG2a. Although the relative titres as compared with BSA and FCA vary with time after the second challenge, and with the different strains, the NISV were capable of achieving an adjuvant effect in all three strains tested, eliciting an antibody response either greater than that produced by BSA/FCA, or at least of a magnitude comparable thereto.

Example 5

Preparation of a Vaccine Against Congenital Toxoplasmosis

Toxoplasmosis is a disease of birds and mammals caused by the protozoan *Toxoplasma gondii*. In non-protected animals the disease is capable of being vertically transmitted from mother to foetus and such transmission can result in foetal death. Protective immunity can however be generated by previous infection, and to a certain extent by vaccination. It is believed that this results from synergy between $CD8^+$ T cells and the Th1 $CD4^+$ subset. The vaccine properties of NISV-entrapped antigens particularly as regards activation of these subsets of T cells were investigated in BALB/c and BALB/K mouse strains as laboratory models.

Mice

Inbred BALB/c and BALB/K mice and outbred Strathclyde A strain mice were maintained under conventional conditions. Mice were used when 8–10 weeks old and each experimental group comprised 5–10 animals.

The brains of strain A mice, infected with the RRA (Beverly) strain of *T.gondii* 12 weeks previously, were used as a source of tissue cysts which were harvested and enumerated as previously described (Roberts and Alexander 1992, Parasitol. 104, 19–23). All experimental infections were by the oral route and the congenital infection model was also as described previously (Roberts and Alexander 1992). Briefly BALB/c mice were infected on days 11–12 of pregnancy with 20 tissue cysts. Surviving offspring were then transferred to infected foster mothers and the incidence of congenital infection measured 8–9 weeks after birth by ELISA. Severity of infection was monitored, where appropriate, by mortality levels or by total cyst counts in the brain.

Antigen Preparations

Freeze-thawed killed tachyzoites (kp), tachyzoite excretory/secretory antigens (ESAg), membrane antigens and soluble antigens (STAg) were all used in vaccination studies. *T.gondii* tachyzoites of the RH strain were obtained from peritoneal exudates of infected cotton rats and washed 3 times in saline. ESAg was obtained by incubating $5 \times 10^{10}$ tachyzoites overnight in 40 mls of PBS. Tachyzoites were removed by centrifugation at 1000 g and the supernatant collected. All protein concentrations were determined by a Bradford assay (Bradford 1976 Analyt. Biochem. 72, 248–254). Tachyzoite soluble and membrane antigen fractions were obtained following disruption of $5 \times 10^{10}$ parasites in hypotonic buffer (40 ml 10 mM Tris-HCl, 2 mM EDTA, pH 7.8) using a Braun homogeniser followed by centrifugation at 10,000 g for 30 mins at 4° C. The supernatant comprised the STAg and the pellet the membrane fraction. The membrane antigens were further purified using 1% octyl glucoside followed by centrifugation at 100,000 g. The supernatant was collected and dialysed overnight against PBS at 4° C. to remove the detergent.

Vaccine Preparations

All animals to receive vaccine preparations were inoculated subcutaneously with 50 µg tachyzoite antigen 2 weeks and 4 weeks before infection. Antigen for vaccination was used either in a free form or emulsified in Freund's Complete Adjuvant or entrapped within non-ionic surfactant vesicles.

Vesicle Formation

STAg entrapment in 1-monopalmitoyl glycerol NISV was achieved by the methods described in Example 1.

Results

Figure 7A:
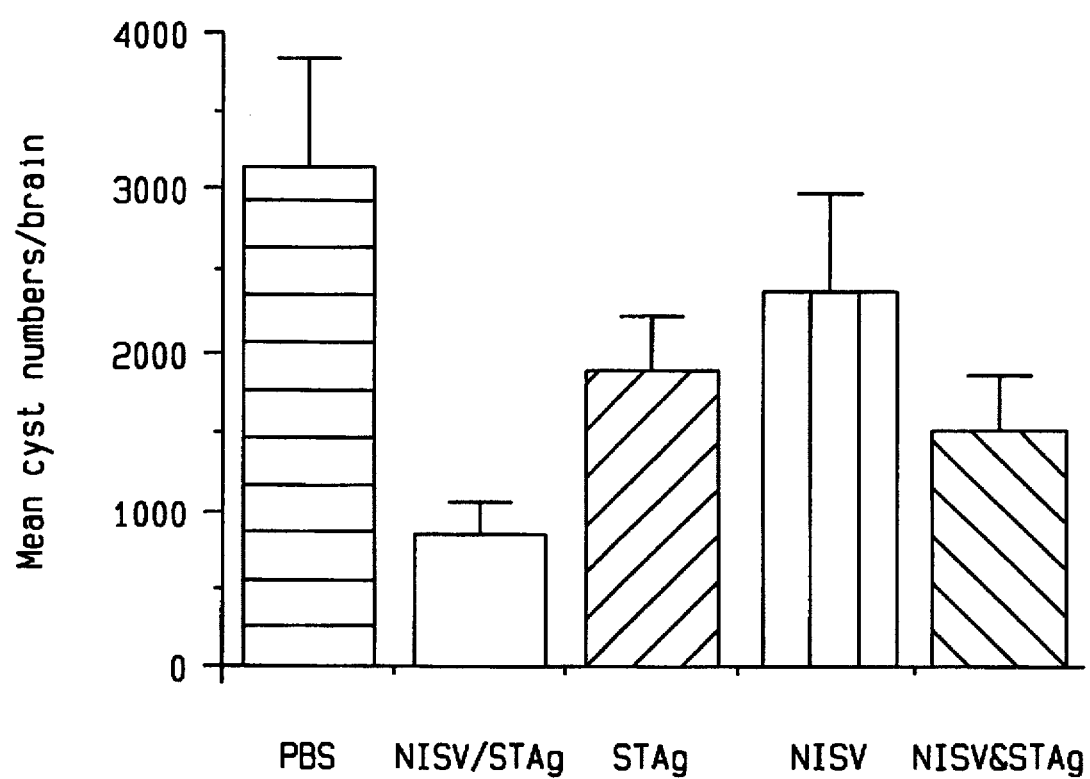
FIG. 7A illustrates the mean number of cysts found in BALB/K mice brains 4 weeks after oral infection for vaccinated and non-vaccinated mice.

The results obtained are shown in FIGS. 7A–D. FIG. 7A shows the mean number of cysts (+/−S.E.) 4 weeks post infection in the brains of BALB/K mice orally infected with 20 cysts following subcutaneous inoculation with STAg entrapped in NISV, alone or when mixed with NISV 2 and 4 weeks prior to infection. As can be seen, STAg entrapped in NISV produced significantly reduced cyst numbers as compared with other groups.

Figures 7B, 7C:
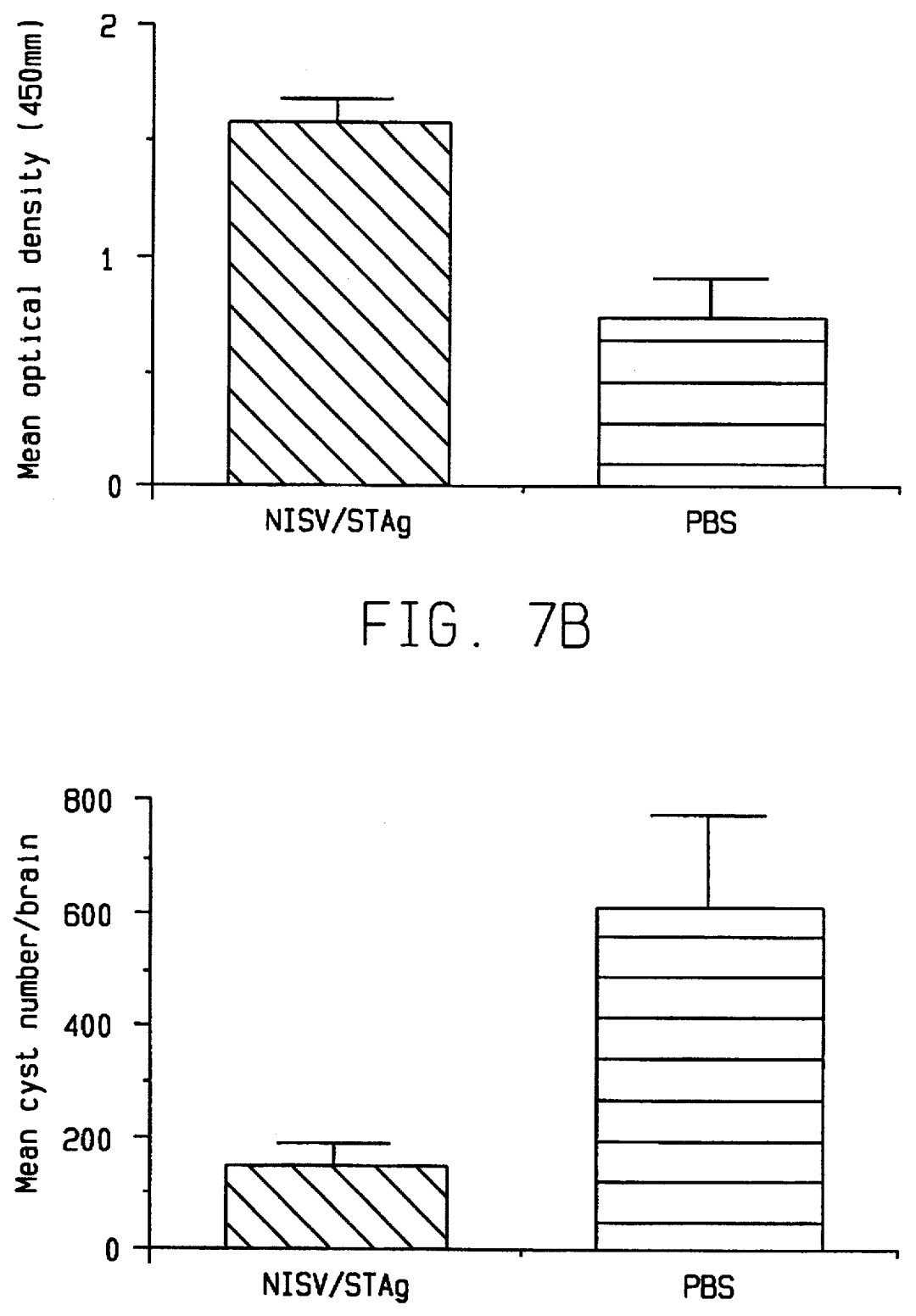

FIG. 7B shows mean serum antibody levels and FIG. 7C shows mean cyst numbers in brains of BALB/c dams 8 weeks after oral infection with 20 cysts. The mice were infected on days 11–12 of pregnancy. The vaccinated group had been inoculated with STAg entrapped in NISV (50 µg) subcutaneously 2 and 4 weeks before infection. As can be seen, vaccination with NISV entrapped antigen significantly reduced both the cyst numbers in brains, and antibody levels, as compared to controls.

Figure 7D:
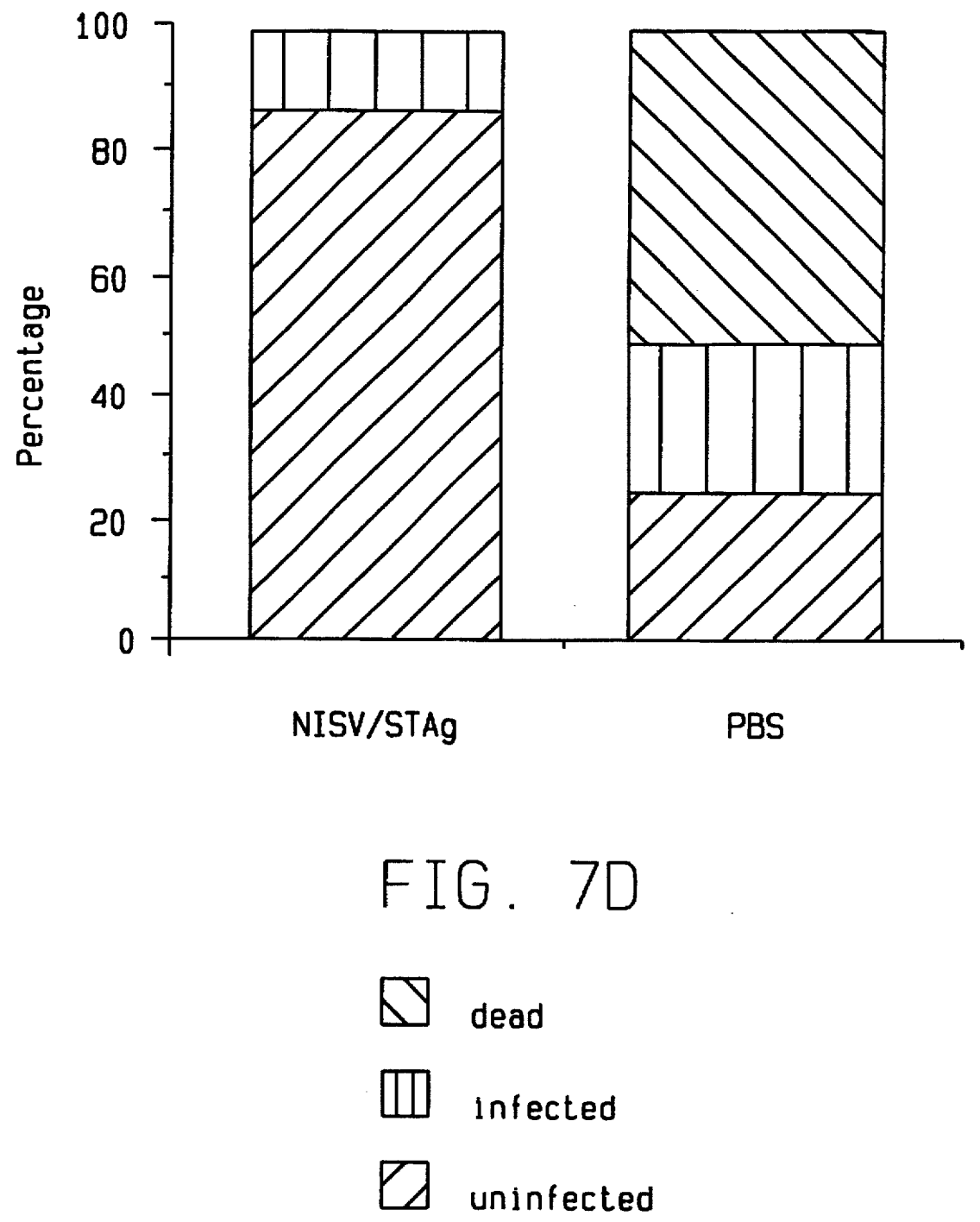

FIG. 7D shows the fate of the pups born to the vaccinated and non-vaccinated mice. As can be seen, no foetal deaths occurred in the pups born to the vaccinated mice as compared to the non-vaccinated sample where more than half the pups were dead at or within 24 hours of birth, despite the fact that over 50% of the offspring born to the vaccinated mice were infected.

Thus we have shown that entrapment of the soluble antigen within NISV promotes an adjuvant effect which enhances the protection of this antigen to adult mice and completely eliminates foetal death.

Example 6

The Ability of NISV to Act as an Adjuvant for Synthetic T Cell Epitopes

Preparation of Peptide

The "Giles" peptide, being residues 258–277 of the measles F protein was synthesised by conventional FMOC chemistry. The peptide has the sequence: (SEQ ID NO:1) GILESRGIKARITHVDTESY and contains both T and B cell epitopes.

The NISV were prepared from 1-monopalmitoyl glycerol ester according to the method of Collins (Supra), and the antigens entrapped using the freeze-thaw technique of Pick (Supra).

Immunisation

Groups of 8–10 week old female BALB/c mice, 4 mice in each group, were immunised subcutaneously with 25 μg of peptide in PBS, entrapped in NISV, or emulsified in FCA. One week later, their spleens were removed and the peptide specific T cell proliferative response measured by thymidine incorporation assay (Corradin et al, J. Immunol. 119, 1048–1053 (1977)).

Results

Figure 8:
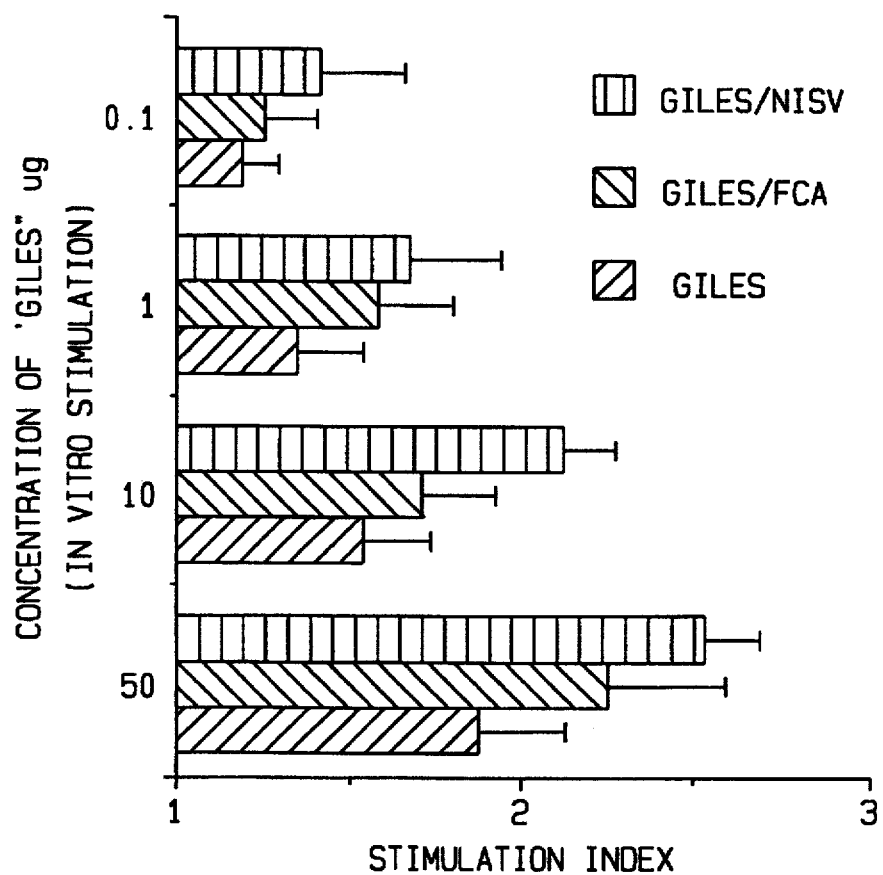
Figure 9:
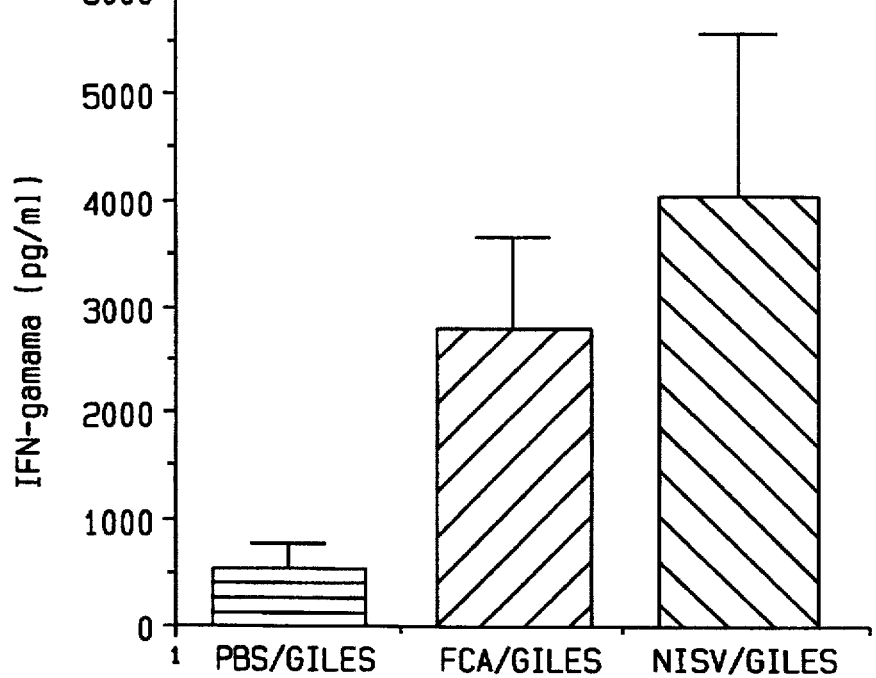

The results are shown in FIGS. 8 and 9. At all concentrations examined in the assay, spleen cells from mice immunised with NISV entrapped antigen proliferated to a greater extent in vitro as compared with the cells derived from mice which received the peptide in PBS or FCA (FIG. 8).

Supernatants from the cultures which had been stimulated with 50 μg/ml GILES were removed 48 hours post stimulation and assayed for the presence of IFN γ by ELISA. As can be seen from FIG. 9, Spleen cells from mice vaccinated with GILES together with an adjuvant produced significantly more IFN-γ than mice vaccinated with GILES in PBS, and NISV-entrapped antigen produced more IFN-γ than antigen in FCA. Thus NISV are capable of acting as an adjuvant for peptides corresponding to larger vital proteins, as well as for hormones. Furthermore, NISV prime the mice for antigen specific T cell proliferation to a greater extent than FCA. The presence of IFN-γ in the culture supernatants implies the activation of CD4+ Th1 cells and/or CD8+ T cells.

Example 7

Oral Delivery Experiment

Oral Administration of BSA entrapped with NISV in mice

Vesicles are formed from either diglycol cetyl ether (DGCE) or 1-monopalmitoyl glycerol ester (MPG), in the ratio 5:4:1 surfactant:cholesterol:dicetyl phosphate as described in Example 1. Vesicles are prepared by rotary film evaporation from chloroform as described by Russell and Alexander (Supra). 150 μmoles of surfactant formed into thin film is hydrated in 5 ml of carbonate buffer containing 100 mg of BSA. The mixture is shaken for 2 hours at 60° C. prior to sonication for 5 mins in a water-bath sonicator also at 60° C.

8–10 week old female BALB/c mice are used with five mice in each treatment group. Each group receives the following:

a) BSA in carbonate buffer
b) BSA in DGCE NISV
c) BSA in MPG NISV

The mice receive a primary oral dose of 0.1 ml (240 μg BSA per mouse) administered by gavage tube on day 1. On day 12, a second oral dose is administered (500 μg BSA per mouse). Blood samples are collected on days 20 and 24 and analysed for IgG titre.

---

What is claimed is:

1. A vaccine comprising at least one antigen entrapped in non-ionic surfactant vesicles, wherein said vesicles enhance the immune response to said at least one antigen.

2. A vaccine as claimed in claim 1 wherein the antigen is a peptide.

3. A vaccine as claimed in claim 2 wherein the peptide is of synthetic or recombinant origin.

4. A vaccine as claimed in claim 3 wherein the peptide contains from 8 to 50 amino acid units.

5. A vaccine as claimed in claim 4 wherein the peptide contains from 10 to 20 amino acid units.

6. A vaccine as claimed in claim 2 wherein the peptide is linked to a carrier.

7. A vaccine as claimed in claim 1 wherein the antigen is selected from antigens of the protozoan *Toxoplasma gondii*, luteinizing hormone release hormone and analogues of luteinizing hormone releasing hormone wherein said analogues have the formula pGlu-His-Trp-Ser-Tyr-X-Leu-Arg-Pro-Gly-Y-Z wherein X represents Gly or a D-amino acid, Y represents one or more amino acid residues, which may be the same or different, and Z represents Cys or Tyr.

8. A vaccine as claimed in claim 1 wherein said non-ionic surfactant comprises a glycerol ester.

9. A vaccine as claimed in claim 8 wherein said glycerol ester is a glycerol monoester comprising $C_{12}$–$C_{20}$ alkanoyl or alkenoyl moieties.

10. A vaccine as claimed in claim 9 wherein the glycerol ester is 1-monopalmitoyl glycerol.

11. A vaccine as claimed in claim 1 wherein the vesicles comprise ethers based on glycerol or a lower aliphatic glycol.

12. A vaccine as claimed in claim 11 wherein the ethers are glycerol monoethers or monoethers based on lower aliphatic glycols comprising $C_{12}$–$C_{20}$ alkanyl or alkenyl moieties.

13. A vaccine as claimed in claim 12 wherein the monoethers comprise up to 5 glycol units.

14. A vaccine as claimed in claim 12 wherein the glycerol ether is 1-monocetyl glycerol ether or the lower aliphatic glycol ether is diglycol cetyl ether.

15. A vaccine as claimed in claim 1 wherein the vesicles additionally comprise charge-producing amphiphilic molecules.

16. A vaccine as claimed in claim 15 wherein the charge-producing amphiphilic molecule contains an acidic group selected from carboxylate, phosphate or sulphate.

17. A vaccine as claimed in claim 1 for subcutaneous, intramuscular or intradermal administration.

18. A vaccine for oral administration comprising at least one antigen entrapped in non-ionic surfactant vesicles wherein said vesicles enhance the immune response to said at least one antigen.

19. A vaccine for mucosal administration comprising at least one antigen entrapped in non-ionic surfactant vesicles wherein said vesicles enhance the immune response to said at least one antigen.

20. An oral vaccine comprising at least one antigen entrapped in non-ionic surfactant vesicles in the form of a syrup or capsule wherein said vesicles enhance the immune response to said at least one antigen.

21. A method for preparing a vaccine comprising entrapping at least one antigen in non-ionic surfactant vesicles, wherein said vesicles enhance the immune response to said at least one antigen.

22. A method of formulating an antigen as an orally-active vaccine comprising entrapping said antigen in non-ionic surfactant vesicles wherein said vesicles enhance the immune response to said antigen.

23. A method of formulating at least one antigen to stimulate antibody production via the Th1 T lymphocyte pathway comprising entrapping said at least one antigen in non-ionic surfactant vesicles wherein said vesicles enhance the immune response to said at least one antigen.

24. A method for potentiating the immunogenicity of at least one antigen to a level at least equal to that obtained by the use of Freund's Complete Adjuvant comprising entrapping said at least one antigen in non-ionic surfactant vesicles wherein said vesicles enhance the immune response to said at least one antigen.

25. A method as claimed in any one of claims 21, 22, 23 or 24 wherein the antigen is entrapped within preformed vesicles.

26. A method as claimed in claim 25 wherein the non-ionic surfactant vesicles with entrapped antigen is orally administered.

27. A method as claimed in claim 26 wherein the vesicles comprise ester-linked surfactant molecules.

28. A method as claimed in any one of claim 21, 22, 23 or 24 wherein said subject is mammalian.

29. A method of potentiating the immunological response to at least one antigen in a subject comprising administering to said subject said at least one antigen entrapped in non-ionic surfactant vesicles wherein said vesicles enhance the immune response to said at least one antigen.

30. A method of potentiating the immunological response to at least one antigen in a subject comprising orally administering to said subject said at least one antigen entrapped in non-ionic surfactant vesicles wherein said vesicles enhance the immune response to said at least one antigen.

31. A method of stimulating cell mediated and/or humoral immunity in a subject in response to at least one antigen comprising administering to said subject said at least one antigen entrapped in non-ionic surfactant vesicles wherein said vesicles enhance the immune response to said at least one antigen.

32. A method of stimulating antibody production via the Th1 T lymphocyte pathway in a subject in response to at least one antigen comprising administering to said subject said at least one antigen entrapped in non-ionic surfactant vesicles wherein said vesicles enhance the immune response to said at least one antigen.

33. A method as claimed in any one of claims 29, 30, 31 or 32 wherein said subject is mammalian.

34. A method as claimed in any one of claims 29, 31 or 32 wherein said entrapped antigen is orally administered.

35. A vaccine comprising at least one antigen entrapped in non-ionic surfactant vesicles, wherein said antigen alone elicits a weak immune response and said vesicles enhance the immune response to said at least one antigen.

36. A method for preparing a vaccine comprising entrapping at least one antigen in non-ionic surfactant vesicles, wherein said antigen alone elicits a weak immune response and said vesicles enhance the immune response to said at least one antigen.

* * * * *